United States Patent
Schels et al.

(10) Patent No.: US 6,670,173 B1
(45) Date of Patent: Dec. 30, 2003

(54) BIOREACTION MODULE FOR BIOCHEMICAL REACTIONS

(75) Inventors: Hans Schels, Munich (DE); Horst Menzler, Herrsching (DE); Ulrike Fischer, Penzberg (DE)

(73) Assignee: Roche Diagnostics GmbH (DE)

( * ) Notice: Subject to any disclaimer, the term of this patent is extended or adjusted under 35 U.S.C. 154(b) by 0 days.

(21) Appl. No.: 09/890,090

(22) PCT Filed: Jan. 21, 2000

(86) PCT No.: PCT/DE00/00190

§ 371 (c)(1),
(2), (4) Date: Jul. 26, 2001

(87) PCT Pub. No.: WO00/44877

PCT Pub. Date: Aug. 3, 2000

(30) Foreign Application Priority Data

Jan. 27, 1999 (EP) .......................................... 99101418

(51) Int. Cl.⁷ .............................................. C12M 1/12
(52) U.S. Cl. ............................ 435/297.2; 435/297.5; 435/297.1; 435/287.2
(58) Field of Search .................... 435/287.2, 289.1, 435/297.1, 297.2, 297.5

(56) References Cited

U.S. PATENT DOCUMENTS

| | | | |
|---|---|---|---|
| 5,478,730 A | | 12/1995 | Alakhov et al. ........... 435/68.1 |
| 5,591,636 A | * | 1/1997 | Grass ..................... 435/287.1 |
| 5,599,688 A | * | 2/1997 | Grass ........................ 435/29 |
| 5,688,687 A | * | 11/1997 | Palsson et al. .......... 435/293.2 |
| 5,888,807 A | * | 3/1999 | Palsson et al. .......... 435/293.2 |

FOREIGN PATENT DOCUMENTS

| | | | |
|---|---|---|---|
| EP | 0894852 A2 | 2/1999 | ............ C12M/1/40 |
| WO | WO92/07062 | 4/1992 | ............ C12M/1/40 |
| WO | WO94/18341 | 8/1994 | ........... C12P/21/02 |

OTHER PUBLICATIONS

Julie Davis, et al. "Large Scale Dialysis Reactions Using *E. coli* S30 Extract Systems" in vitro Transcription/Translation, (8pgs).
Dong–Myung Kim, et al., "A Semicontinuous Prokaryotic Coupled Transcription/Translation System Using a Dialysis Membrane" Biotechnol. Prog. 1996, 12, 645–649.

\* cited by examiner

*Primary Examiner*—David A. Redding
(74) *Attorney, Agent, or Firm*—Kenneth J. Waite; Roche Diagnostics Corporation

(57) ABSTRACT

A bioreaction module for biochemical reactions, in particular for cell-free polypeptide biosynthesis, having a housing (1) including a system chamber (12) and a supply chamber (10), wherein the system chamber (12) contains a producing system during the biochemical reaction and the supply chamber (10) contains a supply liquid during the biochemical reaction, and the system chamber (12) and the supply chamber (10) are separated by a semi-permeable membrane (7).

Figure 1:
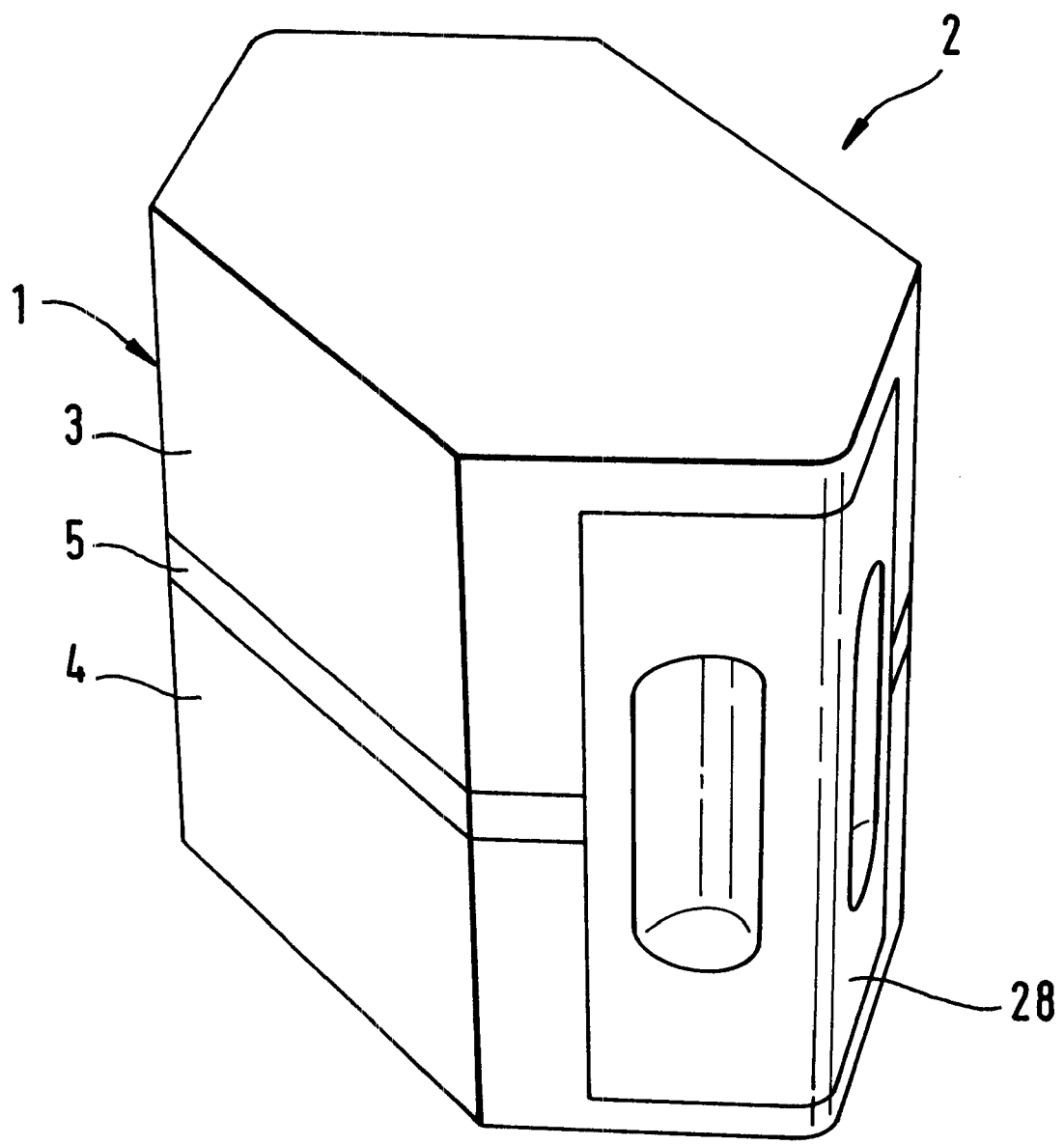

The housing (1) comprises a system chamber element (5) and at least one supply chamber element (3) between which the semi-permeable membrane (7) is mounted in such a manner that the system chamber (12) is defined by the system chamber element (5) and the semi-permeable membrane (7) and the supply chamber (10) is defined by the supply chamber element (3) and the semi-permeable membrane (7).

33 Claims, 4 Drawing Sheets

BIOREACTION MODULE FOR BIOCHEMICAL REACTIONS

The invention concerns a bioreaction module for biochemical reactions, particularly for cell-free biosyntheses of proteins or other polypeptides. For biotechnological applications, biochemical reactions are often carried out in small, easily handled reaction vessels, designated here as bioreaction modules. They primarily serve for the biosynthesis of polypeptides such as peptide hormones, antibiotics and most recently of particular importance, human proteins. Biochemical systems used in such processes include pure translation systems with which the biosynthesis is based on the genetic code of a messenger RNA (mRNA), and transcription/translation systems which also include the preceding step of forming messenger RNA from DNA. In addition to biosynthesis, bioreaction modules are also used for other biochemical reactions, particularly for enzyme reactions.

Cell free biosynthesis is particularly important and has substantial advantages compared to in vivo-systems. For example, it facilitates the expression of toxic and unstable gene products. Cell free synthesis is often used for analytic applications, particularly for rapid and straightforward verification that a desired gene product has actually been synthesized from a cloned gene. There are a plurality of other important applications such as the investigation of protein-:protein interactions and protein:DNA interactions.

A method for cell-free biosynthesis of polypeptides is described e.g. in U.S. Pat. No. 5,478,730. The translation system used therein contains a source of MRNA which encodes the polypeptide. The cell-free synthesis system also contains ribosomes, tRNA, amino acids, ATP and GTP. Translation of the mRNA with the assistance of the tRNA leads to the production of the polypeptide, wherein byproducts and waste products of low molecular weight also simultaneously occur. These can pass into the supply chamber through a semi-permeable membrane which separates the chamber containing the synthesis system from this supply chamber. The supply chamber holds a liquid acting as a supply agent and containing ATP, GTP and amino acids. These components are introduced into the synthesis system through the semi-permeable membrane to replace consumption during the bioreaction. Passage of these components through the semi-permeable membrane is possible, because their molecular weight is less than the molecular cutoff. At the same time, biochemical reaction products and other substances whose molecular weight is below the molecular cutoff of the barrier pass out of the reaction chamber and into the supply chamber. The semi-permeable membrane is, in accordance with U.S. Pat. No. 5,478,730, an ultrafiltration membrane embodied as hollow membrane fibers.

U.S. Pat. No. 5,478,730 contains detailed additional description of suitable compositions for the synthesis system and for the supply liquid. Towards this end, the present invention refers to the previous prior art as, in particular, disclosed in this US patent as well as to the literature cited therein. The complete disclosure of these documents is hereby incorporated by reference.

The components which are biochemically active in biochemical reactions can be designated as the "producing system". To the extent that the invention is utilized for biochemical reactions other than polypeptide syntheses, a producing system is utilized which is appropriate for the associated application. Further details are given in the extensive literature of this art. In principle, a producing system can be any system which is suitable to facilitate or accelerate the production or synthesis of desired compounds using biochemical means. In addition to the translation and transcription systems mentioned, other possibilities include enzyme and enzyme complexes in combination with the conventional auxiliary substances used in methods of this type.

Since the mRNA required for the biosynthesis of polypeptides is usually only available in very small amounts, the bioreaction modules are often very small. The invention is directed, in particular, to micro bioreaction modules with a chamber containing the producing system ("system chamber") having a volume preferentially not in excess of 2 ml but in any event less than 10 ml. Since micro bioreaction modules of this type are disposable products intended for one-time use only, it is particularly important that they be manufactured at low cost.

A particular problem when carrying out biochemical reactions in bioreaction modules is to achieve as high a yield as possible, i.e. as large an amount of product as possible relative to the amount of mRNA used. In order to achieve this goal, U.S. Pat. No. 5,478,730 describes a method known to those of skill in the art as CFCF (continuous flow cell-free) synthesis. In this method, the producing system is enclosed in an ultrafiltration cell and the supply liquid is pumped through the semi-permeable membrane into the chamber in which the producing system is located. In such methods the yield is substantially dependent on the amount of supply liquid fed to the producing system (feed rate) per unit time. For example, U.S. Pat. No. 5,478,730 describes an experiment with a synthesis chamber volume of 1 ml using a feed rate varying between 2 ml/h and 3 ml/h. The results show that the higher feed rate results in a high production efficiency, whereas with the lower feed rate the amount of product increased only negligibly.

The CFCF system facilitates high product yields (in excess of 100 $\mu$g for a system chamber volume of 1 ml). However, there are substantial associated disadvantages. For example, J. Davies et al.: "In vitro Transcription/Translation"; Promega Notes 56, 14–21, criticizes the CFCF method for various problems caused by blockage of the membrane, bothersome protein aggregation and unexplained interruption of the translation. In addition, a complicated apparatus is required. For these reasons, the authors of this publication propose use of the so-called "DispoDialyser®". This is a small tubular vessel having semi-permeable walls in which 250 $\mu$l of the producing system is filled. In order to carry out the biosynthesis, the DispoDialyser is placed in a conical 15 ml test tube which contains between 3.5 and 7 ml of supply liquid. The test tube containing the DispoDialyser is agitated during the reaction time (20 hours) using a laboratory shaking device.

This procedure attempts to avoid the disadvantages of the CFCF method and is intended to facilitate high production yields using relatively simple apparatus. However, these goals are achieved to only a limited extent. In addition, handling is difficult and the quality of the synthesis result is quite irregular. In many cases, leaks or other mechanical damage to the membrane occur which lead to unusable results.

It is therefore an object of the invention to create a bioreaction module with which bioreactions can be carried out in a simple, economical manner to produce as high a yield as possible.

This purpose is achieved with a bioreaction module for biochemical reactions, in particular for cell-free polypeptide biosynthesis, having a housing comprising a system chamber and a supply chamber, wherein the system chamber contains a producing system during the biochemical reaction and the supply chamber contains a supply liquid during the biochemical reaction and the system chamber and the supply chamber are separated by a semi-permeable membrane, characterized in that the housing comprises a system chamber element and at least one supply chamber element and the semi-permeable membrane is mounted between the chamber elements, such that the system chamber is defined by the system chamber element and the semi-permeable membrane and the supply chamber is defined by the supply chamber element and the semi-permeable membrane. The invention is also directed to a bioreaction method using a module of this type.

A bioreaction module in accordance with the invention comprises only a few parts which are easily produced and assembled. Despite the associated low manufacturing costs, it achieves a high yield with simple handling for bioreactions.

The bioreactor in accordance with the invention is suitable for different kinds of bioreaction methods including the continuous flow method. It is, however, preferred for methods in which no pumping is used i.e. in which the supply liquid in the supply chamber is not subjected to external pressure during the biochemical reaction. Consequently, the exchange of substances between the chambers occurs solely by diffusion through the membrane, i.e. dialysis. As the concentrations of substances used up during biosynthesis decreases within the central chamber, those substances flow out of the at least one supply chamber in response to the concentration gradient. The same is true in reverse for biosynthesis waste products.

The semi-permeable membrane is preferentially a dialysis membrane. Dialysis membranes have (for the same molecular cutoff) lower mechanical strength than ultrafiltration membranes utilized in the continuous flow method. Nevertheless, the probability of mechanical damage to the membrane of the bioreaction module in accordance with the invention is very low and, in comparison to an ultrafiltration membrane having the same molecular cutoff, a substantially more effective biosynthesis (better yield) is achieved. The molecular cutoff is preferentially at least approximately 10 kD and at most approximately 20 kD.

For some applications, the housing advantageously includes two supply chambers which border a system chamber and are separated therefrom by a first and a second semi-permeable membrane. The housing of such a three chamber module has two supply chamber elements, wherein the first semi-permeable membrane is mounted between the system chamber element and the first supply chamber element and the second semi-permeable membrane is mounted between the system chamber element and the second supply chamber element.

In accordance with an additional preferred embodiment, at least one and preferentially each of the module chambers contain a magnetic stirring element which can be set into rotation by an external magnetic field. The bioreaction module is a disposable item and can be produced ready for use, optionally including the magnetic stirring element.

The invention is described more closely below on the basis of embodiments represented in the figures.

Figure 2:
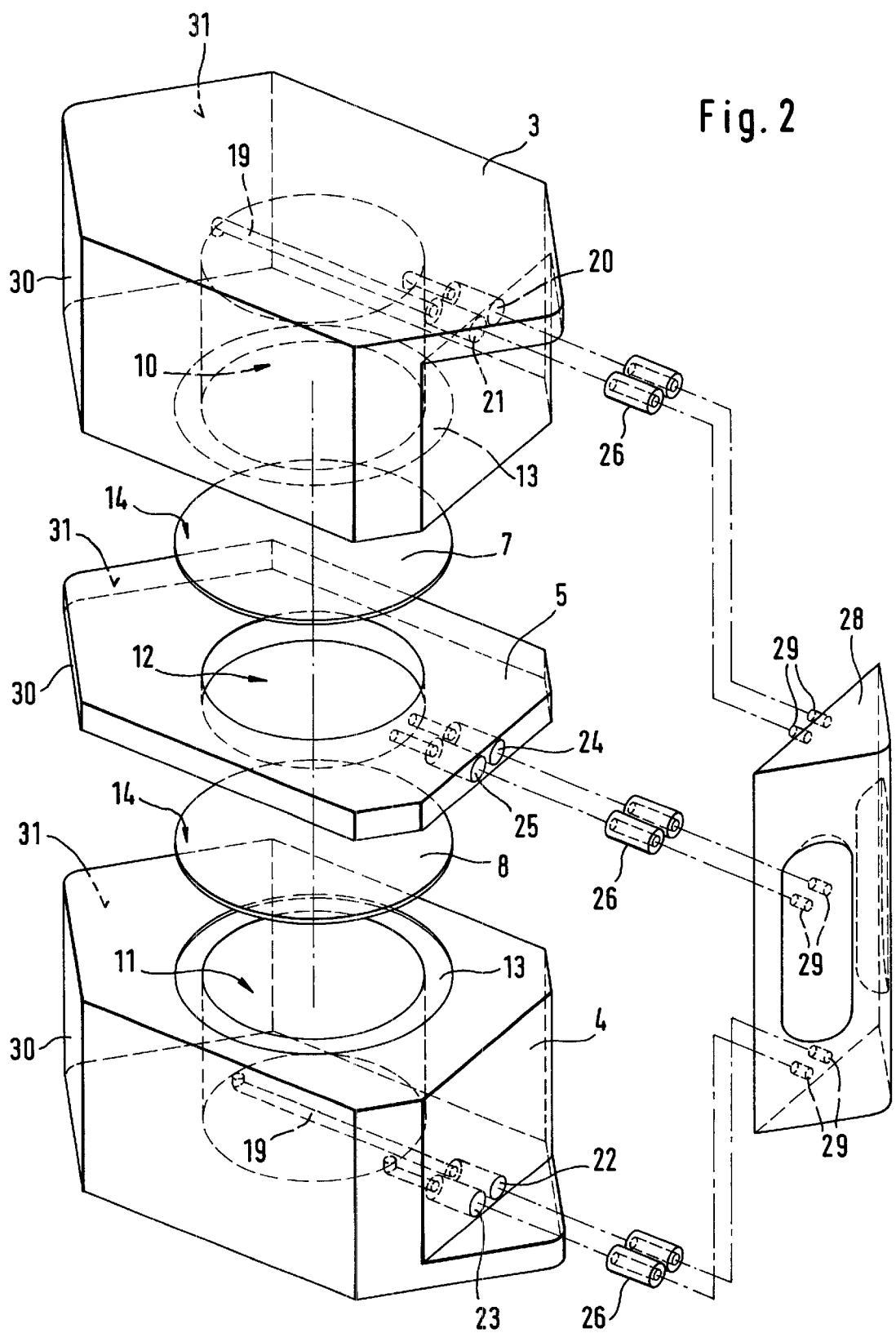
Figure 3:
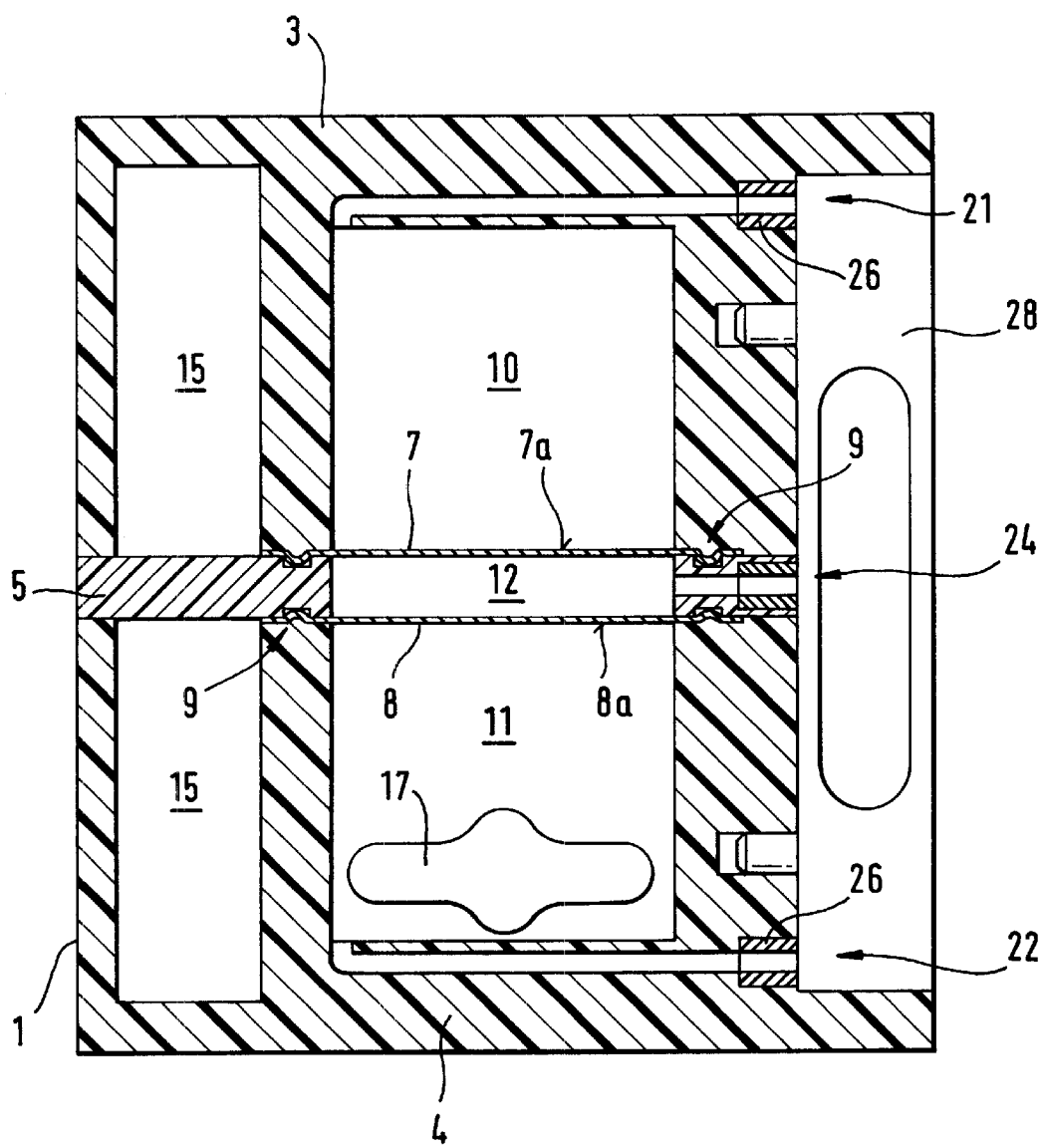
Figure 4:
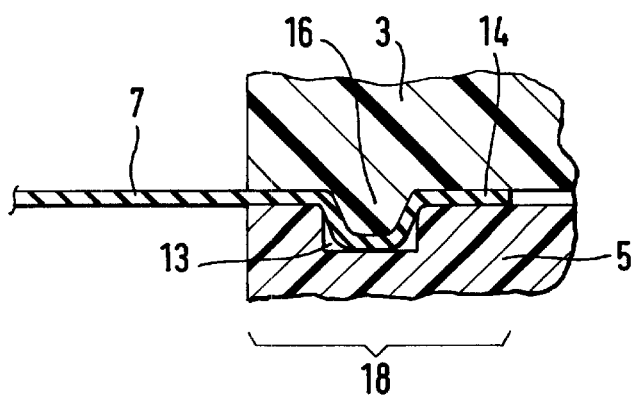
Figure 5:
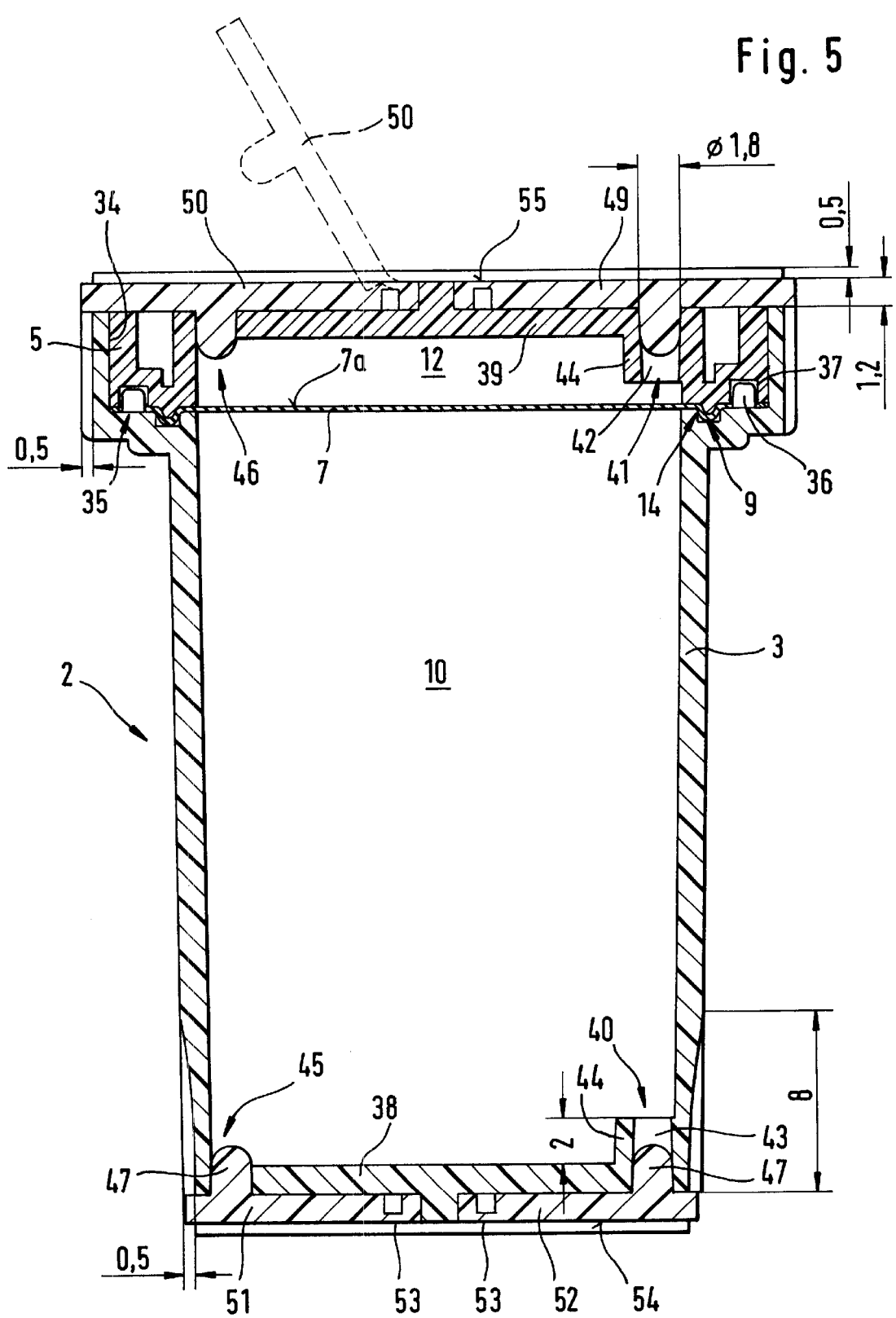

FIG. 1 shows a perspective external view of a bioreaction module in accordance with the invention, FIG. 2 shows an exploded view of the module in accordance with FIG. 1, FIG. 3 shows a cross-section through a slightly different embodiment of a bioreaction module, FIG. 4 shows a detailed view of FIG. 3 to illustrate a preferred structure for securing the edges of a membrane, FIG. 5 shows a cross-section through another preferred embodiment of a bioreaction module in accordance with the invention.

The housing 1 of the bioreaction module 2 shown in FIGS. 1 through 4 consists essentially of three chamber elements, a first supply chamber element 3, a second supply chamber element 4, and a system chamber element 5 disposed between the two supply chamber elements and connected thereto. A first semi-permeable membrane 7 is mounted between the first supply chamber element 3 and the system chamber element 5 in such a fashion that its peripheral marginal section 14 surrounding its exchange surface area is clamped between the adjacent chamber elements 3, 5 to thereby secure the membrane. A second semi-permeable membrane 8 is mounted between the second supply chamber element and the system chamber element in a similar manner.

A first supply chamber 10 is defined by the walls of a recess in the first supply chamber element 3 which is open only in the direction towards the system chamber element 5 and by the first semi-permeable membrane 7, extending over the opening of this recess. A second supply chamber 11 is correspondingly surrounded by the walls of a recess in the second supply chamber element 4 which is likewise opened at one-side and by the second semi-permeable membrane. A system chamber 12 is located between these two semi-permeable membranes 7, 8 and is defined by the two membranes and the walls of a recess in the system chamber element 5 which is open at both sides. The walls of the recesses or cavities in the chamber elements 3, 4 and 5 are aligned, i.e. their edges adjacent to the membranes 7, 8 surround the membranes at a common border line.

The membranes 7, 8 are mounted in a sealed fashion between the chamber elements 3, 5 or 4, 5 respectively in such a manner that a molecular exchange between the system chamber 12 and the neighboring supply chamber 10 or 11 respectively can only occur through the membranes 7 and 8 respectively. The sealing is effected by ring-shaped sealing means 9 provided for on the chamber elements 3, 5 and 4, 5 respectively which surround the exchange surface areas 7a, 8a of the membranes 7, 8 and between which the peripheral marginal area 14 of the membranes 7, 8 is clamped.

A preferred embodiment of suitable sealing means 9 is shown in FIG. 4. In the system chamber 5 shown, one of the chamber elements clamping the membrane comprises a peripheral groove 13 and the other chamber element (in this case the supply chamber element 3) comprises a rib 16 aligned with the groove. Rib 16 penetrates into groove 13 and pushes the peripheral marginal area 14 of the membrane mounted between the chamber elements 3, 5 into the groove 13. The ring-shaped region of the chamber elements 3, 5 at which the marginal area 14 of the membrane 7 is mounted is designated as the mounting region 18. In an embodiment of practical use, the groove 13 has a width of approximately 1 mm and a depth of approximately 0.6 mm. The rib 16 has a height of approximately 0.3 mm, its base width is somewhat smaller than the width of the groove, and its edges penetrating into the groove are, as shown in FIG. 4, rounded.

The chamber elements 3, 4, 5 are preferentially made from plastic such as polyether sulfone, PVC or PMMA and are e.g. produced as molded components. The membrane is made from cellulose acetate and possibly from cellulose nitrate. In an experimental embodiment, the volume of the system chamber was 1 ml and the volume of both the neighboring supply chambers was 5 ml each, so that the ratio of the volume of the system chamber to the overall volume of the supply chambers bordering the system chamber and separated therefrom by a semi-permeable membrane was 1:10. This ratio ranges preferentially between at least 1:5 and at most 1:20, wherein values between at least 1:7 and at most 1:15 are especially preferred.

The chamber elements 3, 4, 5 can be connected by conventional means used in plastics engineering, e.g. by bolting, gluing, or as a plastic plug connection. It is important that the chamber elements 3 to 5 have a stiffness sufficient to guarantee even pressure on the edges of the membrane. In order to reduce weight and to increase the stiffness, the chamber elements can have additional cavities which are not filled with liquids during use of the bioreaction module (e.g. shown as cavities 15 in FIG. 3).

At least one of the chambers preferentially contains a magnetic stirring element 17 which, for reasons of clarity, is only shown in one of the supply chambers of FIG. 3. When a plurality of supply chambers are used, this element is preferentially disposed in both supply chambers. It may also be advantageous to have a magnetic stirring element 17 in all of the chambers, i.e. in the system chamber 12 as well. The bioreaction module 2 is preferentially manufactured and delivered to the user substantially ready for use and optionally including the magnetic stirring elements.

A magnetic stirring element has turned out to be advantageous primarily for use in a supply chamber having a volume in excess of 2 ml, in particular more than 3 ml. For smaller supply chamber volumes (and thereby smaller bioreaction modules), the entire bioreaction module is advantageously agitated by shaking during the biochemical reaction. An agitating ball can thereby be enclosed in at least one of the chambers to improve mixing.

The chambers can be filled using a conventional laboratory pipette. Towards this end, each has a connection opening from which conduits lead into the corresponding chamber. In the embodiment shown in FIG. 2, the supply chambers 10, 11 each have two connection openings 20, 21 and 22, 23 respectively and the system chamber 12 also has two connection openings 24, 25. Seals, e.g. cylindrical silicon rubber seals 26 are provided in the end regions of each of the connection openings to facilitate a sealed connection to the pipette tip. The connection openings 20 to 25 can be closed by a lid member 28 having closing pins 29 which penetrate into the connection openings when the lid member 28 is put into place to effect a sealing closure in cooperation with the seals 26.

In order to carry out a biochemical reaction, the supply chambers 10, 11 are filled with a supply liquid and the system chamber 12 is filled with a producing system. During the biochemical reaction, the at least one magnetic stirring element 17 is set into rotation by an external magnetic field so that the supply liquid or the producing system respectively are continuously stirred during the reaction.

For handling when filling the bioreaction module 2, the housing can be advantageously placed in a position in which the connection openings 20 to 25 are oriented diagonally in an upward direction. This can be achieved when the housing has a base plane extending transverse to the surface of the membrane which is oriented in such a fashion that, when the module is located in the filling position in which the support points lying in the base plane seat on a horizontal surface, the membrane extends substantially vertically such that the connection openings 20 to 25 are located in the upper portion of the module i.e. at least above the center thereof. This position is designated as the fill position. In the module shown in FIG. 2, the diagonally extending surfaces 30 and 31 of the generally rhombic housing each define a base plane which fulfills these conditions. However, the base plane need not be formed by a closed flat housing surface. Since only the orientation of the housing 1 is important, three support points are sufficient to define a base plane fulfilling the mentioned conditions.

For filling purposes, it is advantageous when at least the supply chambers each have a conduit 19 which, when the module is located in the filling position, lead from the corresponding connection opening into the lower region of the respective chamber 10 and 11 and end in the lower region of the chamber, at least below the center thereof.

Although the invention has been described using a three chamber module, other embodiments are also possible having a differing number of chambers, in particular a two chamber module. In this case, the structure of the chamber elements and the mounting of the membrane can be similar to that in the above described figures, wherein the system chamber element is obviously closed at one side (on that side opposite the supply chamber).

FIG. 5 shows such a two chamber module. Components corresponding in function to the above mentioned embodiment have the same reference symbols. The bioreaction module 2 comprises a system chamber 12 and a supply chamber 10. Both chambers are separated from each other by a semi-permeable dialysis membrane 7. The system chamber 12 is defined by a system chamber element 5 and the semi-permeable membrane 7. The supply chamber 10 is defined by a supply chamber element 3 and a semi-permeable membrane 7. The membrane 7 is mounted in a sealed fashion at its peripheral marginal section 14 using a ring-shaped peripheral sealing means 9, wherein the structure described in relation to FIG. 4 is preferentially used.

In order to center and to fix the membrane 7, the embodiment shown provides for a plurality (for example six) of pins 36 distributed about the periphery of and molded onto one of the chamber elements (in this case the supply chamber element 3). The membrane 7 has holes 35 aligned with the pins 36. A slightly conical configuration of the pins 36 and a corresponding dimensioning and positioning of the holes 35 leads to a slight tensioning of the membrane 7 during placement into the chamber element 3 having the pins 36.

In the embodiment shown, the chamber elements 3 and 5 are connected together by pressing the system chamber element 5 into a corresponding receptacle 34 in the supply chamber element 3. In order to guarantee a secure mounting, the outer diameter of the system chamber element 5 is slightly larger than the inner diameter of the receptacle 34.

Each of the chamber elements 3, 5 has a fill opening 40 and 41 for filling the chamber enclosed by the respective chamber element (i.e. the supply chamber 10 and the system chamber 12 respectively). The fill openings 40, 41 each are disposed in a wall 38 and 39 facing away from the membrane 7, preferentially have a round cross-section and pass over into a respective filling channel 42, 43 which is defined by a tubular wall 44 extending into the respective chamber 10 and 12.

The fill channel primarily serves to reduce foaming of the biochemical liquid which is to be filled into the chamber. The bioreaction module shown is designed for applications in which only the fluid which is to be filled into the system chamber 12 has a tendency to foam. To reduce such foaming, its fill channel 42 extends proximate to the membrane 7. The fill channel 43 in the supply chamber 10 is quite short relative to the length of the supply chamber, and is suitable for filling a liquid which does not foam. Should the supply liquid also tend to foam, the fill channel 43 would also extend proximate to the membrane 7.

Each wall 38, 40 disposed opposite to the membrane 7 also has a vent opening 45 and 46 respectively. This preferentially has a shape (e.g. a very narrow slot) which prohibits application of a pipette to prevent unintentional filling through the vent opening.

The fill openings 40, 41 and the vent openings 45, 46 can each be closed by means of a sealing plug 47 which protrudes from flap members 49 to 52 perpendicular to a flat area thereof. The flap members 49 to 52 are hinged for pivoting at each respective wall 38 and 39 opposite the semi-permeable membrane (using inexpensive foil hinges 53) such that the plug 47 sealingly engages into the corresponding openings 40, 41, 45 and 46 when the flap members 49 to 52 are brought into the position shown in FIG. 5. The flap member is pivoted upwardly to open the associated opening, as e.g. shown with dashed lines for the flap member 50.

In the embodiment of FIG. 5, magnetic stirring elements are also preferentially located in the chambers 10, 12 (not shown for reasons of clarity) and are introduced into the chambers when the module 2 is manufactured so that the module has prepackaged magnetic stirring elements 17 and is ready for use when delivered to the user.

The bioreaction module in accordance with the invention allows to perform biochemical reactions in a very effective manner using a relatively small exchange surface area 7a of the membrane 7 in relation to the volume of the corresponding system chamber 12. The ratio of the overall exchange surface area of the membrane or membranes separating the system chamber 12 from the one or more supply chambers to the overall volume of the system chamber 12 is at most 4.0 units$^{-1}$, but should not be below a lower limit of 0.2 units$^{-1}$.

The bioreaction module shown in FIG. 5 allows particularly simple handling without limiting effectiveness. As the dimensions in (mm) given in FIG. 5 indicate, it is extremely small. Each of the walls 38, 39 having the fill openings 40, 41, and preferentially also the vent openings 45, 46, advantageously have a seating surface 54 and 55 respectively which is configured and oriented in such a manner that the respective other chamber 12, 10 can be filled when the module 2 seats on one of the seating surfaces 54 and 55 bordering the respective chamber 10, 12.

With a two chamber module, the configuration shown having two substantially parallel, oppositely positioned surfaces 38, 39 having openings 40, 41, 45, 46 and corresponding flap members 49 to 52 is particularly advantageous. However, these structural elements can also be advantageously used in other configurations of the bioreaction module 2.

We claim:

1. A bioreaction module for biochemical reactions, said module comprising a system chamber, one or more supply chambers, and one or more semi-permeable membranes that allow bidirectional exchange of products and liquids between the system chamber and the one or more supply chambers;

wherein the system chamber is defined by a system chamber element and one or more of said semi-permeable membranes and said system chamber contains a producing system during the biochemical reaction;

wherein each supply chamber is defined by a supply chamber element and one of said semi-permeable membranes which separate the supply chamber from the system chamber and said supply chamber contains a supply liquid during the biochemical reaction;

said module further comprising sealing means engaging a peripheral marginal section of said one or more semi-permeable membranes, said sealing means comprising a peripheral groove in either the supply chamber element or the system chamber element and a protruding rib in the other chamber element for penetrating into the groove to push the membrane at its marginal section into the groove.

2. A module according to claim 1 wherein one of the chamber elements has a fill opening in a wall opposite to the semi-permeable membrane for filling the chamber defined by said chamber element.

3. A module according to claim 2 wherein both the system chamber element and the one or more supply chamber elements have a fill opening for filling the chamber defined by the respective chamber element, that fill opening being located in a wall opposite to the membrane.

4. A module according to claim 3 wherein the walls of the system chamber element and of the supply chamber element containing the fill openings are each configured as seating surfaces for the module and are oriented such that when the module seats on one of these seating surfaces, the other respective chamber can be filled.

5. A module according to claim 2 wherein the wall opposite from the semi-permeable membrane has both a fill opening and an additional vent opening.

6. A module according to claim 1 wherein said one or more semi-permeable membranes is a dialysis membrane.

7. A module according to claim 1 wherein the one or more supply chambers comprises first and second supply chambers bordering the system chamber which are separated from the system chamber by said semi-permeable membranes comprising a first and a second semi-permeable membrane, wherein the first semi-permeable membrane is mounted between the system chamber element and the first supply chamber element and the second semi-permeable membrane is mounted between the system chamber element and the second supply chamber element.

8. A module according to claim 1 wherein the ratio of the volume of the system chamber to the total volume of the one or more supply chambers bordering the system chamber and separated therefrom by means of a semi-permeable membrane is at least 1:5 and at most 1:20.

9. A module according to claim 1 wherein the ratio of the overall exchange surface area of said one or more semi-permeable membranes separating the system chamber from the one or more supply chambers to the overall volume of the system chamber is at least 0.2 units$^{-1}$ and at most 4.0 units$^{-1}$.

10. A bioreaction module for biochemical reactions, said module comprising a system chamber, one or more supply chambers, and one or more semi-permeable membranes that allow bidirectional exchange of products and liquids between the system chamber and the one or more supply chambers;

wherein the system chamber is defined by a system chamber element and one or more of said semi-permeable membranes and said system chamber contains a producing system during the biochemical reaction;

wherein each supply chamber is defined by a supply chamber element and one of said semi-permeable membranes which separate the supply chamber from the system chamber and said supply chamber contains a supply liquid during the biochemical reaction;

said module further comprising sealing means engaging a peripheral marginal section of said one or more semi-permeable membranes, wherein the one or more supply chamber and/or the system chamber contains a magnetic stirring element.

11. A module according to claim 10 wherein said one or more semi-permeable membranes is a dialysis membrane.

12. A module according to claim 10 wherein the one or more supply chambers comprises first and second supply chambers bordering the system chamber which are separated from the system chamber by said semi-permeable membranes comprising a first and a second semi-permeable membrane, wherein the first semi-permeable membrane is mounted between the system chamber element and the first supply chamber element and the second semi-permeable membrane is mounted between the system chamber element and the second supply chamber element.

13. A module according to claim 10 wherein the ratio of the volume of the system chamber to the total volume of the one or more supply chambers bordering the system chamber and separated therefrom by means of a semi-permeable membrane, is at least 1:5 and at most 1:20.

14. A module according to claim 10 wherein the ratio of the overall exchange surface area of said one or more semi-permeable membranes separating the system chamber from the one or more supply chambers to the overall volume of the system chamber is at least 0.2 units$^{-1}$ and at most 4.0 units$^{-1}$.

15. A bioreaction module for biochemical reactions, said module comprising a system chamber, one or more supply chambers, and one or more semi-permeable membranes that allow bidirectional exchange of products and liquids between the system chamber and the one or more supply chambers;
   wherein the system chamber is defined by a system chamber element and one or more of said semi-permeable membranes and said system chamber contains a producing system during the biochemical reaction;
   wherein each supply chamber is defined by a supply chamber element and one of said semi-permeable membranes which separate the supply chamber from the system chamber and said supply chamber contains a supply liquid during the biochemical reaction;
   said module further comprising sealing means engaging a peripheral marginal section of said one or more semi-permeable membranes,
   wherein one of the chamber elements has a fill opening in a wall opposite to the semi-permeable membrane for filling the chamber defined by said chamber element; and
   the fill opening can be closed by a sealing plug which protrudes outwardly from a flap member hinged for pivoting on the wall opposite of the semi-permeable membrane.

16. A module according to claim 15 wherein both the system chamber element and the one or more supply chamber elements have a fill opening for filling the chamber defined by the respective chamber element, that fill opening being located in a wall opposite to the membrane.

17. A module according to claim 16 wherein the walls of the system chamber element and of the supply chamber element containing the fill openings are each configured as seating surfaces for the module and are oriented such that when the module seats on one of these seating surfaces, the other respective chamber can be filled.

18. A bioreaction module for biochemical reactions, said module comprising a system chamber, one or more supply chambers, and one or more semi-permeable membranes that allow bidirectional exchange of products and liquids between the system chamber and the one or more supply chambers;
   wherein the system chamber is defined by a system chamber element and one or more of said semi-permeable membranes and said system chamber contains a producing system during the biochemical reaction;
   wherein each supply chamber is defined by a supply chamber element and one of said semi-permeable membranes which separate the supply chamber from the system chamber and said supply chamber contains a supply liquid during the biochemical reaction;
   said module further comprising sealing means engaging a peripheral marginal section of said one or more semi-permeable membranes;
   wherein the molecular cutoff of the one or more semi-permeable membranes is at least 10 kDalton and not more than 20 kDalton.

19. A module according to claim 18 wherein the one or more semi-permeable membranes is a dialysis membrane.

20. A module according to claim 18 wherein the one or more supply chambers comprises first and second supply chambers bordering the system chamber which are separated from the system chamber by said semi-permeable membranes comprising a first and a second semi-permeable membrane, wherein the first semi-permeable membrane is mounted between the system chamber element and the first supply chamber element and the second semi-permeable membrane is mounted between the system chamber element and the second supply chamber element.

21. A module according to claim 18 wherein the ratio of the volume of the system chamber to the total volume of the one or more supply chambers bordering the system chamber and separated therefrom by means of a semi-permeable membrane, is at least 1:5 and at most 1:20.

22. A module according to claim 18 wherein the ratio of the overall exchange surface area of the one or more semi-permeable membranes separating the system chamber from the one or more supply chambers to the overall volume of the system chamber is at least 0.2 units$^{-1}$ and at most 4.0 units$^{-1}$.

23. A method for carrying out a biochemical reaction comprising using a module as claimed in claim 10 wherein, during the biochemical reaction, the supply liquid is not subjected to external pressure in the supply chamber so that molecular exchange between the one or more supply chambers and the system chamber is substantially due to diffusion, and the producing system and/or the supply liquid is stirred during the biochemical reaction using said magnetic stirring element.

24. A method for carrying out a biochemical reaction comprising using a module according to claims 1 to 22 wherein, during the biochemical reaction, the supply liquid is not subjected to external pressure in the one or more supply chambers so that molecular exchange between the one or more supply chambers and the system chamber is substantially due to diffusion and the bioreaction module is shaken during the biochemical reaction.

25. A method for carrying out a cell-free polypeptide biosynthesis comprising using a module according to claims 1 to 22, wherein, during the biochemical reaction, the supply liquid is not subjected to external pressure in the one or more supply chambers so that the molecular exchange between the one or more supply chambers and they system chamber is substantially due to diffusion through the membrane.

26. A method according to claim 25 wherein the ratio of the volume of the system chamber to the total volume of the one or more supply chambers bordering the system chamber and separated therefrom by means of said one or more semi-permeable membranes is at least 1:5.

27. A method according to claim 26 wherein said ratio of volumes is at most 1:20.

28. A method according to claim 25 wherein said one or more semi-permeable membranes is a dialysis membrane.

29. A method according to claim 25 wherein the molecular cutoff of said one or more semi-permeable membranes is at least 10 kDalton and not more than 20 kDalton.

30. A method according to claim 25 wherein the ratio of the overall exchange surface area of said one or more semi-permeable membranes separating the system chamber from the one or more supply chambers to the overall volume of the system chamber is at least 0.2 units$^{-1}$ and at most 4.0 units$^{-1}$.

31. A bioreaction module for biochemical reactions, said module comprising a system chamber, one or more supply chambers, and one or more semi-permeable membranses that allow bidirectional exchange of products and liquids between the system chamber and the one or more supply chambers;

wherein the system chamber is defined by a system chamber element and one or more of said semi-permeable membranes and said sytem chamber contains a producing system during the biochemical reaction;

wherein each supply chamber is defined by a supply chamber element and one of said semi-permeable membranes which separate the supply chamber from the system chamber and said supply chamber contains a supply liquid during the biochemical reaction;

said module further comprising sealing means engaging a peripheral marginal section of said one or more semi-permeable membranes, wherein the ratio of the volume of the system chamber to the total volume of the one or more supply chambers bordering the system chamber and separated therefrom by means of a semi-permeable membrane is at least 1:5.

32. A module according to claim 31 wherein said ratio of volumes is at most 1:20.

33. A module according to claim 31 wherein the ratio of the overall exchange surface area of said one or more semi-permeable membranes separating the system chamber from the one or more supply chambers to the overall volume of the system chamber is at least 0.2 units$^{-1}$ and at most 4.0 units$^{-1}$.

* * * * *